(12) United States Patent
Burgmeier et al.

(10) Patent No.: US 7,713,233 B2
(45) Date of Patent: May 11, 2010

(54) BALLOONS HAVING A CROSSLINKABLE LAYER

(75) Inventors: Robert Burgmeier, Plymouth, MN (US); Richard L. Goodin, Blaine, MN (US); Joseph Delaney, Jr., Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1648 days.

(21) Appl. No.: 10/822,364

(22) Filed: Apr. 12, 2004

(65) Prior Publication Data

US 2005/0228429 A1    Oct. 13, 2005

(51) Int. Cl.
*A61M 31/00* (2006.01)
*A61M 37/00* (2006.01)

(52) U.S. Cl. ............................ 604/103.06; 604/96.01; 606/191

(58) Field of Classification Search ............... 604/96.01, 604/103.06, 103.07, 103.08; 606/191, 192, 606/194
See application file for complete search history.

(56) References Cited

U.S. PATENT DOCUMENTS

| | | | | |
|---|---|---|---|---|
| 3,719,539 A | 3/1973 | Lamb et al. ............... 156/199 |
| 4,065,589 A | 12/1977 | Lenard et al. ............ 428/34.7 |
| 4,490,421 A | 12/1984 | Levy ....................... 428/34.7 |
| 4,935,190 A | 6/1990 | Tennerstedt .............. 264/529 |
| 4,963,313 A | 10/1990 | Noddin et al. ........... 264/573 |
| 5,026,607 A | 6/1991 | Kiezulas ................. 428/423.7 |
| 5,272,012 A | 12/1993 | Opolski .................. 428/423.1 |
| 5,306,246 A | 4/1994 | Sahatjian et al. ........ 604/96.01 |
| 5,344,400 A * | 9/1994 | Kaneko et al. ........ 604/103.06 |
| 5,348,538 A | 9/1994 | Wang et al. ............ 604/103.12 |
| 5,556,383 A | 9/1996 | Wang et al. ............ 604/103.11 |
| 5,620,649 A | 4/1997 | Trotta ....................... 264/515 |
| 5,714,110 A | 2/1998 | Wang et al. ............... 264/529 |
| 5,766,158 A | 6/1998 | Opolski ..................... 604/265 |
| 5,820,594 A | 10/1998 | Fontirroche et al. .... 604/165.01 |
| 5,824,173 A | 10/1998 | Fontirroche et al. ......... 152/86 |
| 5,830,182 A | 11/1998 | Wang et al. ............. 604/96.01 |
| 5,951,941 A | 9/1999 | Wang et al. ................ 264/523 |
| 5,968,069 A * | 10/1999 | Dusbabek et al. .......... 606/194 |
| 6,083,587 A * | 7/2000 | Smith et al. ............... 428/36.6 |
| 6,146,356 A | 11/2000 | Wang et al. ............. 604/96.01 |
| 6,165,166 A | 12/2000 | Samuelson et al. ......... 604/524 |
| 6,171,278 B1 | 1/2001 | Wang et al. ................ 604/104 |
| 6,406,457 B1 | 6/2002 | Wang et al. ............. 604/96.01 |
| 6,409,863 B1 | 6/2002 | Williams et al. ........... 156/198 |
| 6,464,683 B1 | 10/2002 | Samuelson et al. ......... 604/524 |
| 6,530,938 B1 | 3/2003 | Lee et al. .................. 606/194 |
| 6,557,835 B2 | 5/2003 | Dijk ........................... 261/87 |
| 6,596,818 B1 | 7/2003 | Zamore .................... 525/426 |
| 6,656,550 B1 | 12/2003 | Zamore .................... 428/35.7 |
| 6,897,168 B2 * | 5/2005 | Branham et al. ............. 442/59 |
| 2003/0152728 A1 | 8/2003 | Wang et al. ............... 428/36.9 |
| 2004/0073250 A1 * | 4/2004 | Pederson et al. ........... 606/192 |
| 2004/0093008 A1 | 5/2004 | Zamore .................... 606/194 |

* cited by examiner

*Primary Examiner*—Kevin C Sirmons
*Assistant Examiner*—Bhisma Mehta
(74) *Attorney, Agent, or Firm*—Vidas, Arrett & Steinkraus, P.A.

(57) ABSTRACT

A dilatation balloon for use in combination with a catheter device, the balloon having a waist, cone and body portion and having a first layer formed from a first polymeric composition, the balloon having a second layer disposed on at least a portion of the first layer, the second layer formed from a second polymeric composition which is crosslinked on at least a portion of the dilatation balloon, and methods of making and using the same.

14 Claims, 6 Drawing Sheets

BALLOONS HAVING A CROSSLINKABLE LAYER

FIELD OF THE INVENTION

The present invention relates to the area of catheters for performing medical procedures, and more particularly, to balloon catheters for use in angioplasty procedures.

BACKGROUND OF THE INVENTION

Balloon catheters are commonly used in relatively non-invasive medical procedures for the treatment of heart disease, such as in coronary angiography and percutaneous transluminal coronary angioplasty (PTCA). During such procedures, a balloon catheter is advanced through the vasculature of a patient such that the balloon is positioned proximate a restriction in a diseased vessel. The balloon is then inflated and the restriction in the vessel is opened.

In a typical PTCA procedure, a hollow guiding catheter, a guidewire and a dilation catheter are inserted into the vasculature of a patient. The guiding catheter has a pre-shaped distal tip which is percutaneously introduced into the vasculature and advanced. An operator, such as a surgeon, twists and moves the proximal end of the guiding catheter to advance the distal tip through the aorta. The distal tip reaches the ostium of a diseased coronary artery.

Such medical devices require exacting specifications in order to perform adequately under the rigorous conditions in which they are required to perform. Depending on the end use, such medical devices may be primarily comprised of polymeric materials that are non-thrombogenic, non-immunogenic, flexible, manipulatable, that exhibit both radial and longitudinal strength and/or, in certain applications, and so forth.

Balloon dilatation catheters desirably have strength, softness, flexibility and a thin, low profile which are important for achieving the performance characteristics of folding in an uninflated state, tracking, crossing and recrossing the area of the obstruction or stenosis in a vessel in an uninflated state. However, when balloon dilatation catheters are used in large vessels, such as in the coronary or peripheral systems, the size of the vessels and thus the size of the balloons used to dilate them requires that the balloons have a thicker wall. Thicker walls however, tend to increase the stiffness, and to decrease the ability to track, and to cross and recross, for example.

Thus, inasmuch as there are very few single polymeric materials that provide this combination of characteristics, most medical devices are comprised of more than one polymeric material to provide the desired combination of physical properties. The use of multiple polymeric materials, in turn, requires that the polymeric materials be securely bonded together, through welding or through the use of an adhesive, or other bonding method.

Thus, adhesives or thermal welding are typically employed in several locations of a balloon catheter. For instance, balloon catheters typically have an outer tubular member with a distal extremity terminating within the balloon interior and an inner tubular member with a distal extremity extending through and slightly beyond the distal end of the balloon. The annular space between the inner and outer members defines the inflation lumen in communication with the balloon interior. The integrity of the balloon interior is maintained, thereby enabling the balloon interior to hold inflation media, by fluid tight bonds located at proximal and distal extremities of the balloon which secure the balloon to the outer tubular member and the inner tubular member respectively.

Additionally, it may be desirable to form a guide catheter by bonding together two or more tubular sections in order to achieve a more rigid proximal portion and more flexible distal portion. Thus, when a guide catheter is comprised of more than one generally tubular section, these sections are joined together at joints where the distal end of a first tubular section is affixed to the proximal end of a second tubular section.

Thus, in the manufacture of balloon catheters or guide catheters, a number of techniques may be used to bond the balloon to the catheter shaft, including use of adhesives or thermal bonding, i.e. welding.

During welding operations, it is common to employ a heat shrinkable material as a way to exert a compressive force on the region to be welded. Polyolefin or polytetrafluoroethylene heat shrink are typically used in the manufacture of medical devices as a way to exert force and thermally weld two polymeric materials together. See, for example, commonly assigned U.S. Pat. No. 6,409,863 which is incorporated by reference herein in its entirety.

Using a heat shrink material is accomplished by a multi step process including irradiating the heat shrink and then expanding the material to achieve the required compressive properties typically accomplish this. The heat shrink is then cut in to small rings and placed around the surfaces to be bonded or welded. Placement and orientation of the heat shrink is very important to the production of an acceptable and reproducible bond. Thus, this method is both time consuming and costly. See also commonly assigned U.S. Pat. No. 5,549,552 which is incorporated by reference herein in its entirety.

There remains a need in the art to employ polymeric materials in such a way as to optimize the performance of various components of a catheter device, and for a faster, more economical process for joining various components of a catheter device Additionally, there remains a specific need in the art for a dilatation balloon catheter which has an improved crossing profile and stenosis recrossing, trackability, and balloon retrieval after deflation.

SUMMARY OF THE INVENTION

In one aspect, the present invention relates to selection application of a crosslinkable layer to a medical device, such as a balloon catheter.

In one aspect, the invention relates to application of a crosslinkable layer over overlapping regions of two polymeric materials which are to be welded or otherwise bonded together. The crosslinkable layer is irradiated to form a highly crosslinked polymer structure such that the crosslinked layer compresses the bonded or welded region.

In one embodiment, the crosslinkable layer is formed on the waist portion of the expandable member of a balloon catheter to form an integral heat shrink layer which is employed to exert a force for thermal welding of the balloon to the catheter shaft over which it is fitted.

In this embodiment, the crosslinkable layer may be irradiated such that a crosslinked area of high density is formed resulting in the required compressive properties during welding of the balloon to the shaft.

In another aspect, the present invention relates to a balloon and to a method of making the same wherein the balloon exhibits improved trackabiltiy, cross and recross and rewrapping characteristics by forming a crosslinkable layer on at least a portion the balloon. For example, tracking can be improved by forming a crosslinkable layer on the balloon cones and then irradiating the crosslinkable layer such that when the balloon is collapsed, the now crosslinked layer puts compressive force on the balloon cones such that the balloon structure will more easily collapse.

More specifically, in one embodiment of the present invention relates to a dilatation balloon for use in combination with a catheter device. The balloon having waists, cones and a body portion. The balloon includes a first inner layer formed from a first polymeric composition and a second outer layer formed from a second polymeric composition which is disposed over at least a portion of the balloon structure. The second polymeric composition is crosslinkable such that upon irridation or by other chemical means, the polymeric composition crosslinks such that it will form regions of compression on the balloon structure.

In one embodiment, the second composition is disposed on the waists only. In this fashion, it can be employed as a heat shrink layer to compress a balloon on a shaft to provide compressive force during welding of the balloon to the shaft. The second layer may then be removed once the balloon has been secured to the catheter shaft.

In another embodiment, the second crosslinkable layer is disposed on the cone portion of the balloon. Once crosslinked, the layer can provide a compressive force on the balloon cones. This can improve the tracking, cross and recross, and rewrap characteristics, particularly in large balloons used in the coronary or peripheral venous systems of the body which are typically made with thicker walls which also makes them more difficult to collapse and remove from the vasculature.

The crosslinkable layer may be disposed on both the waist and the cones, the portion on the waist being removed once the balloon is secured to the catheter shaft. It is desirable that the crosslink density on the waist be higher than on the cones.

The crosslinkable layer may be removed if desired using any method known in the art, such as by skiving, removal with a laser system, and so forth, once the components have been satisfactorily secured.

In yet another embodiment, the crosslinkable layer is disposed about the entire first layer. In this embodiment, the second crosslinkable layer may be selectively crosslinked only on the waist and/or cone portions as discussed above such that compression occurs only in these regions of the balloon by irradiating only in specific areas. "This would result in the entire body portion of the balloon being uncrosslinked." Or, the amount of crosslinking may be controlled across the length of the balloon by varying the intensity and/or time of irradiation.

If the entire layer is crosslinked, it is desirable that the crosslink density be higher on the cones than on the body. For example, the ratio of crosslink density on the body of the balloon to the cones may be from about 1:1 to about 1:5.

Selective crosslinking according to the present invention may be accomplished in any number of ways including controlling irradiation, by adding inhibitors at only intermittent portions of the balloon such as in the body, or by applying the crosslinkable material only intermittently along a tubular member. This can be accomplished using intermittent extrusion techniques as well, or other techniques known in the art. Some alternative techniques of application are discussed in commonly assigned U.S. Pat. No. 6,557,835.

Crosslinking may be initiated using any means known in the art and may be chemical such as with catalysts, or by application of an energy source, or both. Photochemistry involves the absorbtion of radiant energy which induces or modifies chemical changes. This process may be further altered through the use of photoinitiators which can increase the rate of chemical change. Chemical changes, e.g. crosslinking, may be initiated by high energy actinic radiation such as electron beam (EB) or ion beam (IB), or by ultraviolet radiation (UV) in the wavelength range of 190-400 nm, for example. Lasers operating in the UV range may thus be employed. Photoinitiators may optionally be added to the monomers, oligomers or polymers to be crosslinked in order to increase the rate of crosslinking. Photoinitiators are typically added in small amounts of about 0 to about 2 wt-%, although this is illustrative only.

In the case of chemical initiation, peroxides such as hydrogen peroxide, hydroperoxides such as cumene hydroperoxide and dicumene hydroperoxide, m-chloroperoxybenzoic acid, acetyl peroxide, and so forth may be dispersed in the polymeric heat shrink layer in which crosslinking is desired.

The amount of crosslinking or crosslinking density may be controlled as desired by varying the amount of chemical agent added, by controlling the intensity of the energy source applied, by controlling the amount of time the energy source is applied, and so forth.

A tie layer may be optionally employed between the first layer and the second crosslinkable layer. Tie layers may be used to improve the adhesion or welding between two otherwise different polymeric compositions which are not miscible or compatible with one another. A tie layer is miscible with and/or chemically interacts with each of the layers and is thus selected based on its compatibility or miscibility and/or reactivity with the polymers to which it comes into contact. In some cases, the tie layer may include a blend of materials.

A tie layer may include any polymer or blend of polymeric materials which is compatible with both layers or may include polymers or other components therein which chemically interact with the layers.

Examples of tie layers which may be employed include, for example, polymers which have been modified with functional groups including, but not limited to, maleic anhydride, epoxies, oxazolines, carbodiimdies, isocyanates, and so forth. Of course, the tie layer is selected based on the polymer compositions which it is being disposed between.

Of course, tie layers may be provided between the balloon and the shaft to which it is being secured as well.

One method of application for both the tie layer and the crosslinkable polymeric material is by intermittent coextrusion of the tie layer and/or heat shrink layer while the tubular parison from which the balloon is made is continuously extruded.

If a tie layer is employed, the crosslinkable layer may be removed by using a lower melting point polymer in the tie layer which upon application of heat becomes flowable, allowing easy removal of the crosslinkable layer if desired.

A crosslink inhibitor such as a free radical scavenger may also be employed in the tie layer in order to prevent crosslinking of the tie layer and facilitate removal.

In some embodiments, the tubular parison in turn is formed into a dilatation balloon by conventional blow molding techniques known in the art. In such embodiments, the balloon may be formed from a polyolefin, polyamide, e.g. nylon, polyester, polyurethane, polyvinyl chlorides, polyethers, and so forth as well as copolymers and terpolymers thereof, and mixtures thereof. Hereinafter, the term "copolymer" shall be used to refer to any polymer formed from two or more monomers.

More specific examples of such balloon materials include, but are not limited to, polyethylene, polyethylene terephthalate, polybutylene terephthalate, polyether-block-copolyamides available under the tradename PEBAX® from Atofina, polyester-polyether block copolymers, and so forth.

In one particular embodiment, the balloon is formed from a polyether block copolyamide (PEBAX®) and the crosslinkable heat shrink material is polyethylene. In this particular embodiment, a tie layer is employed. Examples of materials suitable for use in the tie layer include, polyethylenes modified with maleic anhydride, epoxide groups, oxazolines, carbodiimides, isocyanates, and so forth. Materials suitable for use in the tie layer are described in copending U.S. patent application Ser. No. 10/822,581 (U.S. Patent Publication No. US 2005-0227087 A1) which is incorporated by reference herein in its entirety.

In another aspect, the present invention relates to a method of manufacturing tubular parisons used in the formation of dilatation balloons for balloon catheter assemblies.

In one embodiment, a tubular parison is extruded using a base polymeric composition. A layer may be applied at intermittent intervals to the base tubular parison. The tubular parison may further be processed by conventional blow molding techniques to form a balloon. Such techniques are discussed in more detail in the Detailed Description following.

In one embodiment, the crosslinkable layer is formed on the waist portion of the balloon. In this embodiment, the crosslinkable layer may be used as a heat shrink layer during disposition of the balloon about the catheter shaft. Disposition and placement of the crosslinkable layer may be accomplished during extrusion of the tubular parison using intermittent coextrusion techniques, for example, although other techniques of application such as spraying, painting, and so forth, may also be employed.

After extrusion of the tubular parison and application of the crosslinkable layer on it, crosslinking may be induced. Crosslinking may be accomplished in any of a variety of ways depending on the polymeric material which is employed. For example, crosslinking may be induced by application of an energy source, such as actinic radiation, which is absorbed by the polymer. Examples of actinic radiation include, for example, electron beam or ion beam, or a UV energy source such as a laser.

Photoinitiators may be optionally employed.

Crosslinking may also be induced chemically through the use of catalysts, for example, such as free radical generating peroxide such as hydrogen peroxide, m-chloroperoxybenzoic acid, acetyl peroxide, or the like, may be added to the composition to initiate crosslinking.

The tubular parison may then be further processed/molded into a balloon.

Orientation of the crosslinkable layer in order to achieve compressive strength may also be accomplished during the balloon molding process to improve the intimate contact with the crosslinkable layer and to eliminate defects such as bubbling, misalignment, and so forth.

Any of a variety techniques known in the art may be employed for balloon formation. An extruded parison may be radially expanded as is into a mold or by free-blowing. Alternatively, the parison may be pre-stretched longitudinally before expansion or reformed in various ways to reduce thickness of the balloon cone and waist regions prior to radial expansion. The blowing process may utilize pressurization under tension, followed by rapid dipping into a heated fluid; a sequential dipping with differing pressurization; a pulsed pressurization with compressible or incompressible fluid, after the material has been heated. Heating may also be accomplished by heating the pressurization fluid injected into the parison.

Balloon forming techniques may be found in U.S. patent application Ser. No. 10/753,043 (U.S. Patent Publication No. US 2005-0146085 A1), or in U.S. Pat. No. 449,042, Levy, U.S. Pat. No. 4,963,313, Noddin et al, U.S. Pat. No. 5,306,246 Sahatjian, U.S. Pat. No. 4,935,190, Tennerstedt, U.S. Pat. No. 5,714,110, Wang et al., each of which is incorporated by reference herein in its entirety.

During this process, the body, waist and cone portions all expand, but the cones and the waist obviously to lesser degrees. Consequently, the crosslinkable layer also expands.

The now formed balloon is then disposed about the catheter shaft. During bonding or welding, the now crosslinked layer on the waist, which has a memory of sorts, compresses the balloon waist onto the catheter shaft, thus resulting in more intimate contact, and consequently a better bond between the balloon and the shaft.

In this embodiment, a higher level of crosslink density is desired.

Once welded, the heat shrink can be removed by any conventional means known in the art for removing heat shrinkable materials such as by skiving or by removal with a laser.

In one embodiment, a tie layer which is miscible and/or chemically interacts with the layers is employed. A polymeric material having a lower melting temperature than the balloon material may be used such that upon application of heat, the tie layer and thus the overlying crosslinked layer, may be easily removed.

In another embodiment, the crosslinkable layer is applied to the tubular parison such that when the balloon is blow molded, the heat shrinkable material is disposed about the cone region. The crosslinkable layer is then crosslinked. The crosslinking density of this type of application is desirably less than that wherein the crosslinkable layer is applied to the waist and later removed.

Once the balloon has been deflated after use in the venous system, it is more easily removed from the vasculature of the patient because the crosslinkable heat shrinkable material on the cone regions facilitates collapse of the balloon due to its crosslinked structure. This application improves balloon trackability, cross and recross and rewrapping. This is particularly advantageous for larger balloon structures.

In any of the above described embodiments, the second layer comprising the crosslinkable material, may be applied to the entire surface of the tubular parison. The crosslinking can be limited to certain regions through the use of any number of techniques such as by application of an inhibitor to portions of the tubular parison.

If the objective is to facilitate joining together of two or more components or substrates, a heat shield may be used to expose only the bonding regions and the heat shrinkable material overlapping the bonding region. Integrally incorporating the heat shrink into the tubular parison provides an more economical and competitive advantage by reduction of costs and the elimination of several RI and manufacturing steps.

Other advantages and will become apparent from the following Detailed Description.

DETAILED DESCRIPTIONS OF THE PREFERRED EMBODIMENTS

While this invention may be embodied in many different forms, there are described in detail herein specific embodiments of the invention. This description is an exemplification of the principles of the invention and is not intended to limit the invention to the particular embodiments illustrated.

Figure 1:
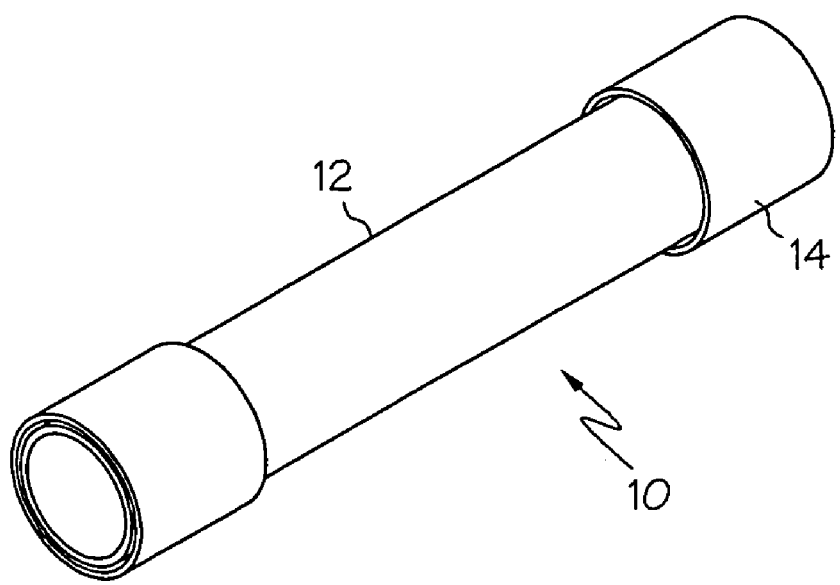
FIG. 1 is a three dimensional view of a tubular parison having an integral heat shrink layer according to the invention.

Turning now to the figures, FIG. 1 illustrates a base extruded tubular parison 12 formed from a first polymeric composition that has been manufactured using continuous extrusion of the base tubular parison 12 with intermittent extrusion of a crosslinkable layer 14. The crosslinkable layer is 14 is shown around each end of the tubular parison 12. Note that this tubular parison 12 is in the trimmed state. In actual production the ends could be longer if desired.

Figure 2:
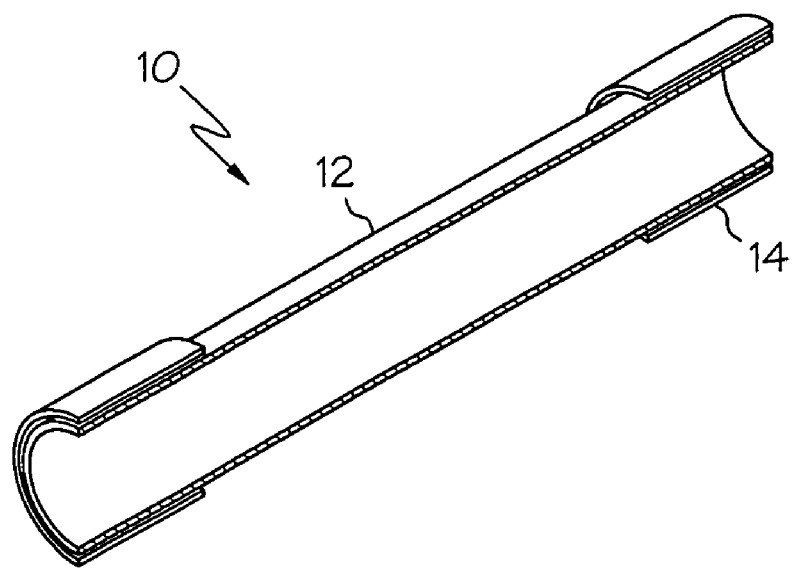
FIG. 2 is a cross sectional view of a similar tubular parison to that shown in FIG. 1.

FIG. 2 is a cross sectional view of the same tubular parison 10 shown in FIG. 1 showing the base layer 12 defining the tubular parison and the crosslinkable layer 14. Crosslinking of layer 14 may be initiated as described above.

The tubular parison may be formed using any conventional techniques known in the art. One method is to extrude the tubular parison continuously, while using intermittent extrusion techniques that would specific placement of the crosslinkable material at specific intermittent locations along the tubular parison. Thus, when the tubular parison was cut into specified lengths for further processing into a balloon, for example, it would allow placement of a heat shrink layer, i.e. in a tubular shape, at each end of the tubular parison. The tube may be further processed to form a dilatation balloon using any methods known in the art as described above.

In this embodiment, the crosslinkable layer may be employed as a heat shrink layer such as those typically used during welding or bonding of the balloon.

In the prior art, heat shrink is typically extruded as a tube, crosslinked, expanded, and then the tube cut into small tubes. The balloon is placed over the catheter shaft such that the waist portion overlaps the shaft, and the heat shrink then placed over this and heated during welding of the balloon to the shaft.

Forming the crosslinkable layer right on the tubular parison according to the invention, reduces the complexity of the manufacturing process.

Crosslinking may be initiated using any suitable means known in the art and of course is dependent upon the crosslinkable polymeric composition employed. Crosslinking may be initiated either through the use of an energy source, or it may be initiated chemically, such as through the use of a catalyst(s), or both.

Radiant energy which can be used includes actinic radiation such as EB, IB or UV, i.e. a laser source. Photoinitiators may be optionally added.

Photopolymerization initiators may be optionally employed in order to increase the rate of crosslinking. Examples of photopolymerization initiators include, but are not limited to, those which contain organic peroxides, s-triazine derivatives, benzophenone or its derivatives, quinones, N-phenylglycine, alkylarylketones, α-aminoketones, α-hdyroxyketones such as benzophenone, benzion ethers, dialkoxy acetophenones, phenylglyoxylates, diazonium salts as a radical generators, and so forth.

Some specific examples include, but are not limited to, 2,4,6-trimethylbenzoyl-diphenyl phosphine, 2-methyl-1-(4-methylthio)phenyl-2-morpholinoporpan-1-one, 1-hydroxy-cyclohexylphenylketone, 4-(4-methylphenylthiophenyl) phyelmethanone, phenyltribomomethylsulphone, 2-isopropyl thioxanthone and r-isopropyl thioxanthone, ethyl 4-(dimethylamino) benzoate, methyl phenylglyoxylate, methyl benzoylbenzoate, 4-methylbenzophenone, benzophenone, and so forth. These photoinitiators are available from Chemik Co. Ltd. under the tradename of KEMICURE®.

Other examples include bis(2,4,6-trimethylbenzoyl)-phenylphosphineoxide, 1-hydroxy-cyclohexylphenylketone, 2-hydroxy-2-methyl-1-phenyl-1-propanone, methylbenzyolformate, 2-benzyl-2-(dimethylamino)-1-[4-(4-mropholinyl)-1-propanone, diphenyl(2,4,6-trimethylbenzoyl)-phosphine oxide, and so forth, available under the tradename of IRGACURE® from Ciba Specialty Chemicals.

This list is intended for illustrative purposes only, and is not intended to limit the scope of the present invention. Such initiators are known to those of ordinary skill in the art.

Crosslinking agents such as catalysts may be added to the crosslinkable layer in order to chemically initiate the crosslinking reaction in sit. Examples of suitable catalysts include, but are not limited to, peroxides such as hydrogen peroxide, m-chloroperoxybenzoic acid, acetyl peroxide, hyper peroxides, and so forth and mixtures thereof. The addition of such crosslinking agents is desirable because crosslinking through the use of an energy source requires an additional step in the manufacturing process. Examples of such crosslinking agents are intended for illustrative purposes only, and are not intended to limit the scope of the present invention. Other agents may be employed without departing from the scope of the present invention.

The above embodiments are intended for illustrative purposes only, and are not intended as a limitation on the scope of the present invention.

The crosslinking density can be controlled by adjusting extrusion conditions, as well as by controlling the intensity of the radiant energy and time that it is irradiated for, as well as by varying the amount of chemical agent which is added.

The flexibility of this process allows for selective and differential manipulation of the crosslinking in order to provide different compressive forces depending on the reason for which crosslinkable layer is provided. For example, suitably, it is desirable to have higher crosslink density and thus higher compressive force on the waist portion of the balloon when the crosslinkable layer is used as a heat shrink versus a lesser crosslink density on the cones wherein the purpose is to facilitate collapse of the balloon structure after use.

The tubular parisons shown in FIGS. 1 and 2 above, can then be further processed/molded into a balloon member for a balloon catheter assembly.

The tubular parison may be processed to form a dilatation balloon using conventional balloon molding techniques. Balloons are typically made by a process by extruding the balloon material into the tubular preform, blow molding the balloon, and then heat setting, i.e. annealing the balloon. The tubular preform may also be stretched prior to blowing. Techniques of balloon formation are described in U.S. Pat. No. 4,490,421, Levy and U.S. Pat. No. 5,348,538, Wang et al., both of which are incorporated by reference herein in their entirety. However, balloon formation is not limited to the techniques described therein, but may be accomplished using any techniques known to those of ordinary skill in the art.

An extruded parison may be radially expanded into a mold or by free-blowing. Alternatively, the parison may be pre-stretched longitudinally before expansion or reformed in various ways to reduce thickness of the balloon cone and waist regions prior to radial expansion. The blowing process may utilize pressurization under tension, followed by rapid dipping into a heated fluid; a sequential dipping with differing pressurization; a pulsed pressurization with compressible or incompressible fluid, after the material has been heated. Heating may also be accomplished by heating the pressurization fluid injected into the parison.

Such balloon forming techniques may be found in U.S. patent application Ser. No. 10/753,043 (U.S. Patent Publication No. US 2005-0146085 A1), U.S. Pat. No. 4,963,313, Noddin et al, U.S. Pat. No. 5,306,246 Sahatjian, U.S. Pat. No. 4,935,190, Tennerstedt, U.S. Pat. No. 5,714,110, Wang et al., each of which is incorporated by reference herein in its entirety.

During this process, the body, waist and cone portions all expand, but the cones and the waist obviously to lesser degrees. Consequently, the crosslinkable layer also expands. The amount of compressive force is dependent, not only on how much crosslinking takes place, but on the amount of expansion or stretching of the crosslinked layer as well.

Orientation of the crosslinkable layer in order to achieve compressive strength may also be accomplished during the balloon molding process wherein the balloon itself is oriented. This can improve the intimate contact with the crosslinkable layer and to eliminate defects such as bubbling, misalignment, and so forth.

Figure 3:
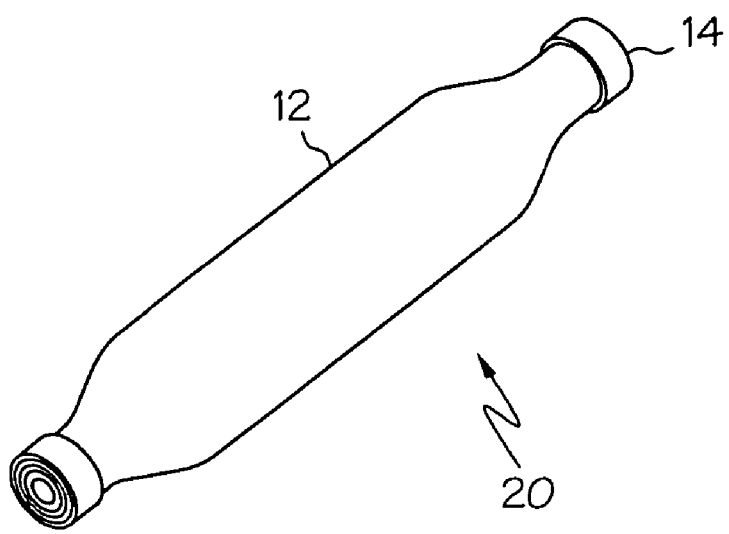
FIG. 3 is a perspective view of a dilatation balloon according to the invention.

FIG. 3 is a representation of a balloon 20 formed by further processing of the tubular parisons shown in FIGS. 1 and 2 by, for example, a blow molding as described above. Balloon 20 is shown with the crosslinked layer 14 on its waist portions 22.

The balloon may then be fitted at the waist portion 22 over a catheter shaft (not shown). During welding or otherwise securing the balloon 20 to a catheter shaft, the crosslinkable layer is heated resulting in compression of the layer around the waist 22 of the balloon 20 which overlaps the catheter shaft.

If the crosslinkable layer 14 is employed for bonding/welding operations between components of a medical device, for example between the balloon and shaft, once the bonding or welding operation is complete, the crosslinkable layer 14 may be removed by any method known in the art for removal of heat shrink system or a laser system such as by skiving off the heat shrink.

Any suitable materials may be employed in the formation of the tubular parisons herein and include both elastomeric and non-elastomeric thermoplastic materials. Thermosetting polymers and moisture curable polymers may be employed as well. If the tubular parisons are further formed into dilatation balloons, any material suitable for dilatation balloons may be employed herein.

Examples of useful classes of materials include, but are not limited to, polyolefins, polyesters, polyethers, polyamides and nylons, polyimides, polyketones, polyphenylene sulfides, polysulfones, polyvinyl chlorides, fluoropolymers such as ePTFE, and mixtures thereof. This also includes any copolymers and terpolymers of such materials. Hereinafter, any polymer formed from more than one monomer shall be referred to as a copolymer. Such materials are known to those of skill in the art. This list is for illustrative purposes only, and is not seen to limit the scope of the present invention.

Block copolymer elastomers are discussed in commonly assigned U.S. Pat. No. 6,406,457, U.S. Pat. No. 6,171,278, U.S. Pat. No. 6,146,356, U.S. Pat. No. 5,951,941, U.S. Pat. No. 5,830,182, U.S. Pat. No. 5,556,383, all of which are incorporated by reference herein in their entirety.

Suitable materials are described in commonly assigned U.S. Pat. No. 5,348,538, the entire content of which is incorporated by reference herein.

Intermediate compliant balloons may be formed from polyethylene (high density, medium density, low density, ultra low density) and nylon materials, for example. Typically, medium to higher density polyethylenes are more suitable for use than those of the low and ultra low density variety.

Non-compliant balloons can be formed from materials such as polyethylene terephthalate (PET), polyimides, polyamides, polyesters, polycarbonates, polyphenylene sulfides, polypropylenes, polyurethanes, and so forth. These materials are typically classified as non-compliant materials which are relatively rigid or stiff polymeric materials.

Highly compliant balloons are made from relatively soft or flexible polymeric materials. Examples of these materials are thermoplastic polymers, thermoplastic elastomers, polyethylene (high density, intermediate density, low and linear low density, ultra low density), various copolymers and blends of polyethylene, ionomers, polyesters, polyurethanes, polycarbonates, polyamides including the Nylons such as Nylon 12, polyvinyl chloride, acrylonitrile-butadiene-styrene copolymers, polyether-polyester copolymers, and polyether-polyamide copolymers. A suitable copolymer material, polyolefin material is available from E. I. DuPont de Nemours and Co. (Wilmington, Del.), under the trade name Surlyn® Ionomers.

Other polymers which may be employed in balloon forming and not specifically classified above, include, for example, polytetrafluoroethylene (PTFE), tetrafluoro ethylene (TFE), polyvinylidine fluoride (PVDF), polyethylene naphthalenedicarboxylate (PEN), and so forth. Materials such as fluoropolymers like PTFE, for example, may find utility as low friction linings or coatings, for example.

Some of the more typical materials include, for example, polyethylene terephthalate, polyamides such as nylon, polyether-block-amides (PEBAX), polyester-polyether block copolymers, and so forth. Dilatation balloons typically have at least two profiles including a noninflated profile, an inflated, non-distended working profile as well as a stretched inflated profile which is achieved by applying pressure through a dilatation catheter or the like that is in excess of that needed to achieve the inflated, non-distended profile and which is adequate to effect dilatation or the like up to a maximum pre-bursting pressure application. The maximum pre-bursting size of the balloon can be tailored depending upon the needs of the particular balloon within a wide range of possible maximum pre-bursting sizes.

Any suitable polymer which crosslinks using the above-described techniques may be employed in the crosslinkable layer. Suitable examples include, but are not limited to, polyolefins such as polyethylene, fluoropolymers such as polytetrafluoroethylene (PTFE), polyamides, any copolymers thereof, and mixtures thereof.

In one embodiment, a crosslinkable polyethylene is employed as the crosslinkable polymer along with a dicumene hydroperoxide catalyst illustrated by the following:

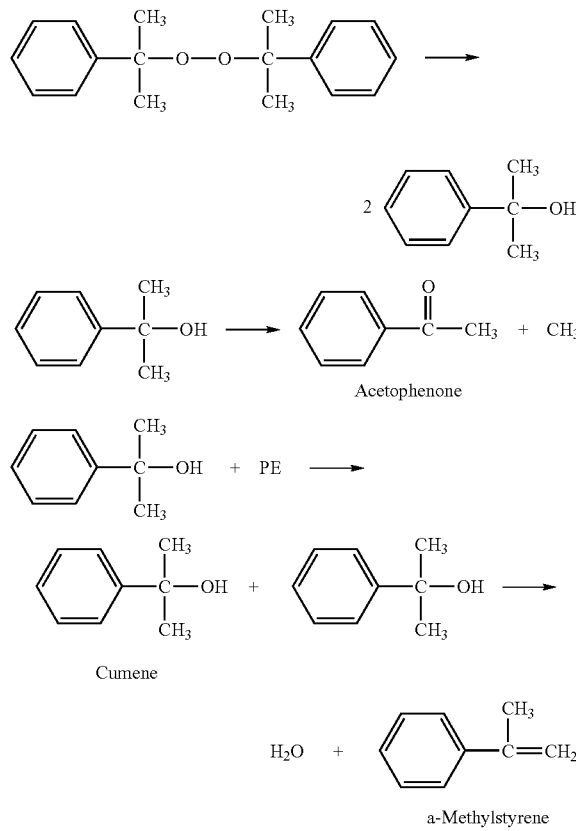

Cumene a-Methylstyrene

A tie layer may optionally be incorporated between the crosslinkable layer and the base layer in any of the embodiments described herein. Incorporation of a tie layer is particularly advantageous where two different polymeric compositions having little compatibility or miscibility with one another are employed. Examples of materials suitable for use in the tie layer include, but are not limited to, maleic anhydride, epoxies, oxaline, carbodiimides, isocyanates, peroxides, and so forth. Such materials can be employed in relatively low amounts of 5 wt-% or less in order to achieve satisfactory results. Such tie layers are discussed above, and are disclosed in copending U.S. patent application Ser. No. 10/822,581 (U.S. Patent Publication No. US 2005-0227087 A1) which is incorporated by reference herein in its entirety.

The following illustrates a tie layer which may be employed in combination with a polyamide or nylon material base material and a polyethylene heat shrink. A melt modified polyethylene may be functionalized by inclusion in the melt of 10-20%, total weight basis, of maleic anhydride and an effective amount of a catalyst such as a phosphate catalyst, e.g. triphenyl phosphite. The resultant carboxylic acid reacts with the polyamide or nylon base material which forms the tubular parison and is miscible with the outer polyethylene heat shrink layer, for example, thus providing a tie layer between two otherwise incompatible, immiscible materials.

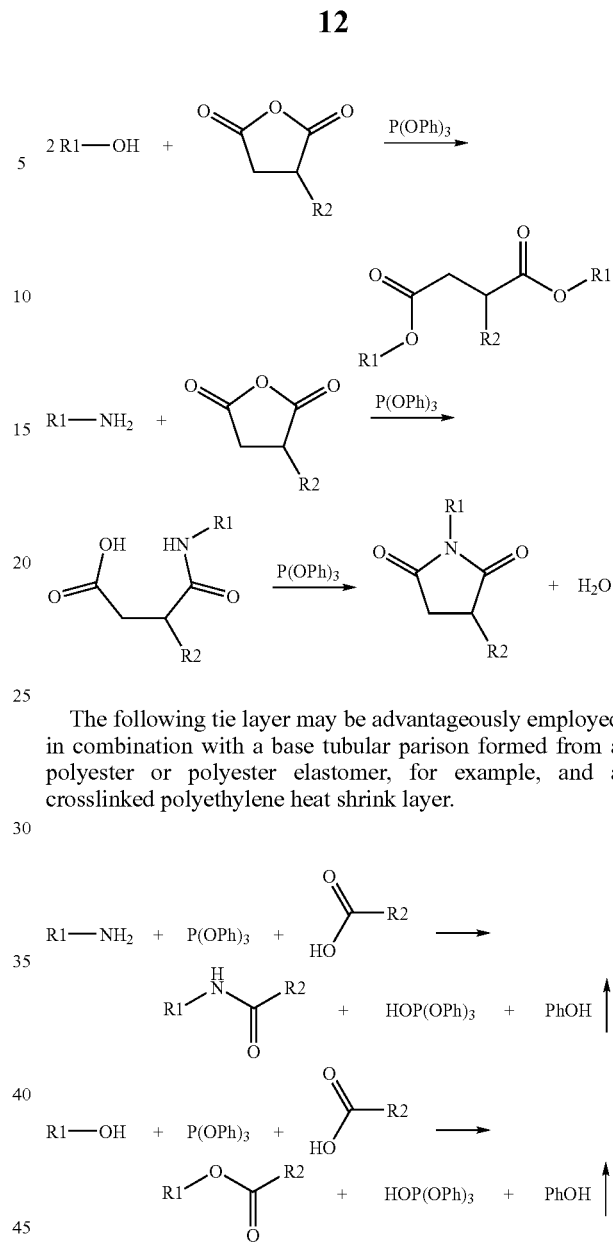

The following tie layer may be advantageously employed in combination with a base tubular parison formed from a polyester or polyester elastomer, for example, and a crosslinked polyethylene heat shrink layer.

In one embodiment, a polyurethane may be employed in the formation of either the first layer or of the second crosslinkable layer. In this case, it may be beneficial to employ an isocyanate in the tie layer. Such materials may be employed in amounts of not more than 5 wt-% to achieve satisfactory results.

Tie layers may operate by chemical interaction with the adjacent layer such as through the formation of covalent bonds, or they may simply be miscible or compatible with the polymeric compositions, and forming a mixture of sorts, at the interface between the tie layer and the polymeric composition upon welding of the joint, for example. Tie layers are known in the art. Specific types of tie layers are described in copending U.S. patent application Ser. No. 10/822,581 (U.S. Patent Publication No. US 2005-0227087 A1), which is incorporated by reference herein in its entirety.

If the crosslinkable layer is employed as a heat shrink on the waist of the balloon during bonding/welding of the balloon to the catheter shaft, it may be beneficial to select a tie layer having a lower melting temperature than the base polymer from which the balloon is formed such that when the bond/weld is heated, the tie layer melts, and the crosslinked outer layer may be easily removed.

A crosslink inhibitor, such as a free radical scavenger, for example, may also be employed in the tie layer to prevent crosslinking of the layer such that it can be easily removed in the above fashion.

The above lists of materials are intended for illustrative purposes only and are not intended to limit the scope of the present invention. Other materials and combinations of materials not specifically discussed herein and known to those of ordinary skill in the art may also be employed herein without departing from the scope of the present invention.

Figure 4:
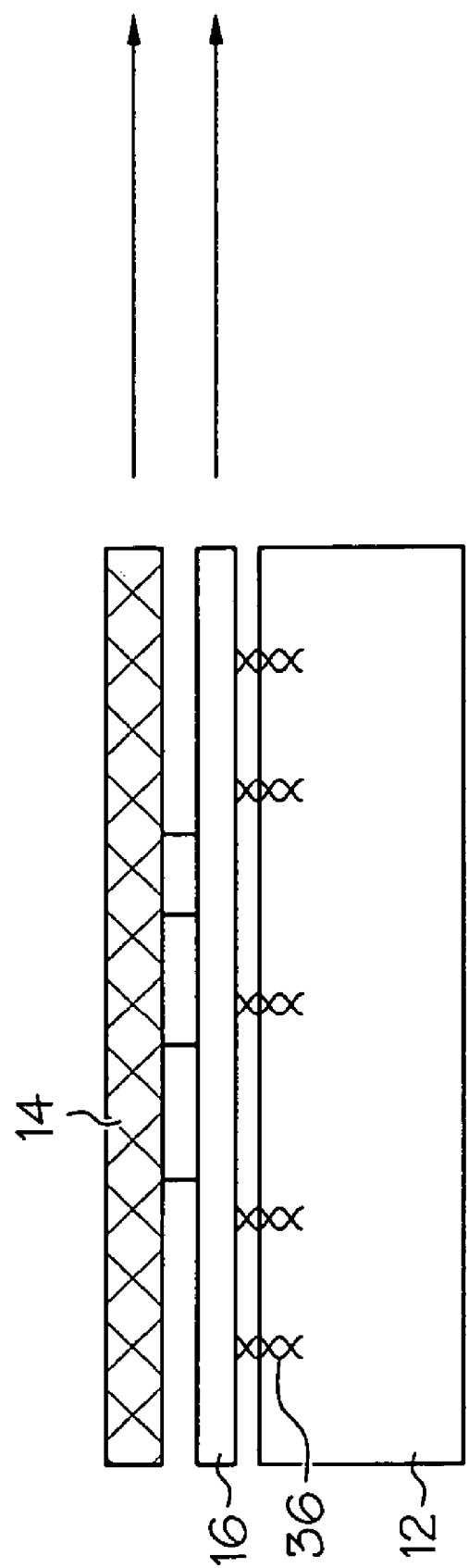
FIG. 4 is a side schematic view of a multilayer structure according to the invention.

FIG. 4 is a side schematic view of a multilayer structure according to the invention having a tie layer 16 shown in between base layer 12 and crosslinkable layer 14. The tie layer in this embodiment is shown having functional groups 36 at the interface of the base layer 12 and the tie layer 16.

A specific example of this type of multilayer structure may include a polyester, polyestery copolymer such as polyethylene terephthalate (PET), polyamide or polyamide copolymer such as a polyamide block ether in the base layer 12, for example, crosslinked polyethylene in the crosslinkable layer 14 and a polyethylene modified with functional groups such as maleic anhydride in the tie layer.

Figure 5:
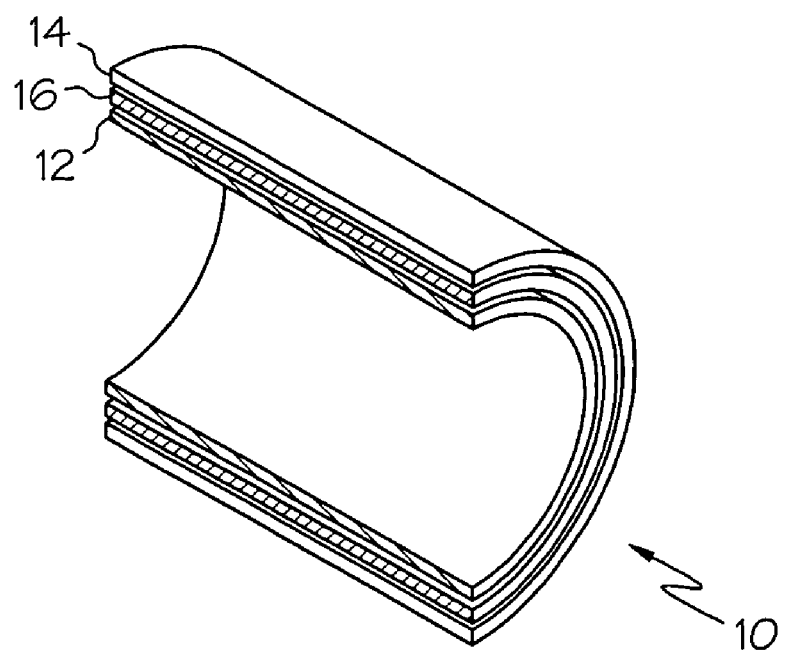
FIG. 5 is a sectional perspective view of a tubular parison having a multilayer construction.

FIG. 5 is sectional perspective view of a multi layer tubular parison 10 in accordance with the invention further having a tie layer 16 between the base polymeric composition 12 and crosslinkable layer 14. In this embodiment, tubular parison 10 has a coextruded three layer construction comprising an inner layer 12 which defines the tubular parison, formed e.g. of PET, an outer heat shrink layer 14, formed e.g. of a crosslinked polyethylene, and a tie layer 16, formed e.g. of melt modified polyethylene. The melt modified polyethylene may be functionalized by inclusion in the melt of 10-20%, total weight basis, of maleic anhydride and an effective amount of a catalyst such as a phosphate catalyst, e.g. triphenyl phosphite. This type of tie layer is described in copending U.S. patent application Ser. No. 10/822,581 (U.S. Patent Publication No. US 2005-0227087 A1) which is incorporated by reference herein in its entirety.

The tubular parison described in FIG. 5 may be further processed using conventional balloon molding techniques as described above into a dilatation balloon 20, such as that shown in a cross sectional perspective view in FIG. 8, described below. In this embodiment, a tie layer 16 is shown between the base layer 12 defining the balloon structure, and the crosslinkable 14 shown on the waist 22 and cone 24 portions in this embodiment.

The crosslinkable layer 14 on the cone 24 desirably has less crosslink density than that on the waist portions 22 which act similarly to a heat shrink layer as described above.

The crosslinkable layer 14 on the cones 24 facilitates collapse of the balloon for removal from the vasculature after use. These balloons have been found to exhibit better trackability, cross and recross and better rewrap characteristics.

For purposes of this description, the ability to cross is defined as the ability of the dilatation balloon of a balloon dilatation catheter to pass through a stenosis; the ability to recross is defined as the ability of the balloon of a balloon dilatation catheter to pass through a stenosis more than once, or to pass through more than one stenosis; and the ability to track is defined as the ability of balloon of a balloon dilatation catheter to pass over a guidewire through the tortuous curves of the vasculature, in being guided to and from the location of a stenosis.

Figure 6:
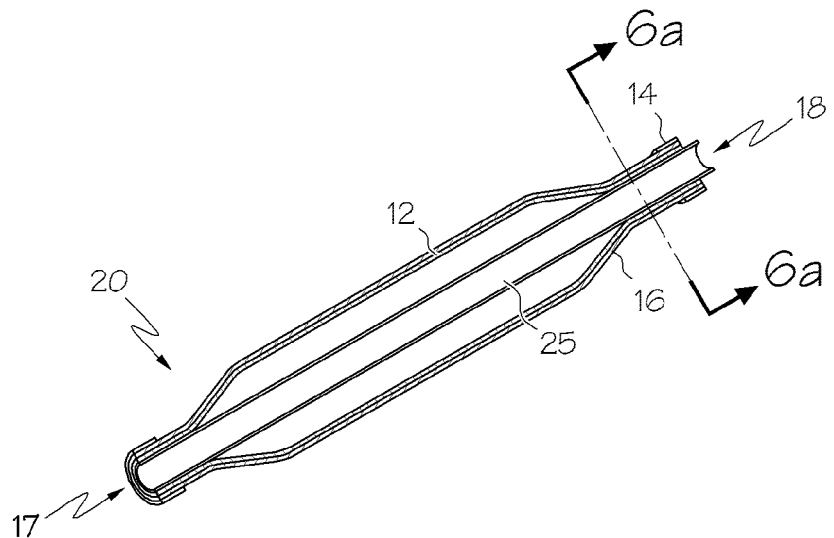
FIG. 6 is a sectional perspective view of a balloon, prepared from a parison as in FIG. 1, mounted on a catheter shaft.
Figure 6A:
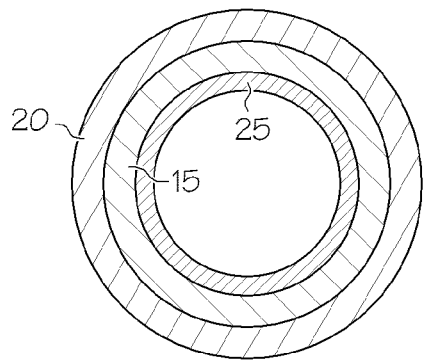
FIG. 6a is a radial cross-section illustrating a balloon mounted on a catheter shaft similar to that shown in FIG. 6 and a tie layer between the balloon and the catheter shaft.

FIG. 6 is a fragmentary sectional view of a balloon 20 which is shown bonded to a catheter shaft 25 at the distal end 17 and the proximal end 18. In this particular embodiment, balloon 20 is made from a tubular parison which is formed from a first base layer 12 defining the balloon structure which includes a first polymeric composition such as polyether block amide available in a variety of grades under the tradename of PEBAX®. The balloon structure could also be a multilayer structure. Distal end 17 is shown with an crosslinkable layer 14 according to the invention and proximal end 18 is shown with an crosslinkable layer 14 according to the invention. Crosslinkable layer 14 may be polyethylene which is crosslinked through application of an energy source such as electron beam radiation or UV, or crosslinking may be chemically induced by adding a crosslinking agent such as a peroxide or hydroperoxide as discussed above. As noted on page 6, lines 1-3, another tie layer 15 may be included between the balloon 20 and the catheter shaft 25 to facilitate bonding therebetween as shown as a radial cross-section in FIG. 6a. Balloon layers are not shown in FIG. 6a.

Figure 7:
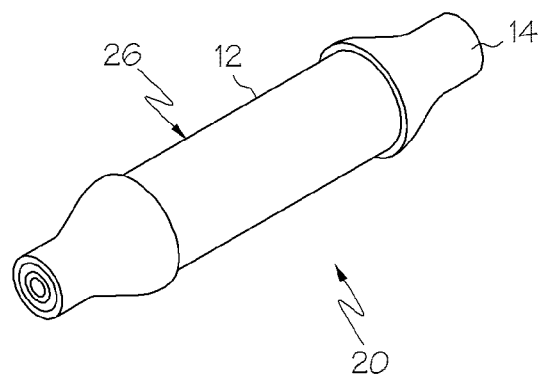
FIG. 7 is a perspective view of a balloon having an integral crosslinked layer on the cone portions.

FIG. 7 is a perspective view of another embodiment according to the invention. In this embodiment, tubular parison according to the invention, has been further process into a balloon 20 according to the invention. Balloon 20 has a waist 22, cones 24 and body portion 26 and is formed of a base layer 12 of a first polymeric composition, and further has a crosslinkable layer 14 formed from a second crosslinkable composition which is shown in this embodiment only on the waist 22 and cone 24 regions of the balloon. The crosslink density on the cones 24 is desirable less than that on the waist portions 22. This can be controlled through intensity and time if a radiant energy source is being applied, or by the amount of chemical agent which is added in the case of chemical catalysis.

Figure 8:
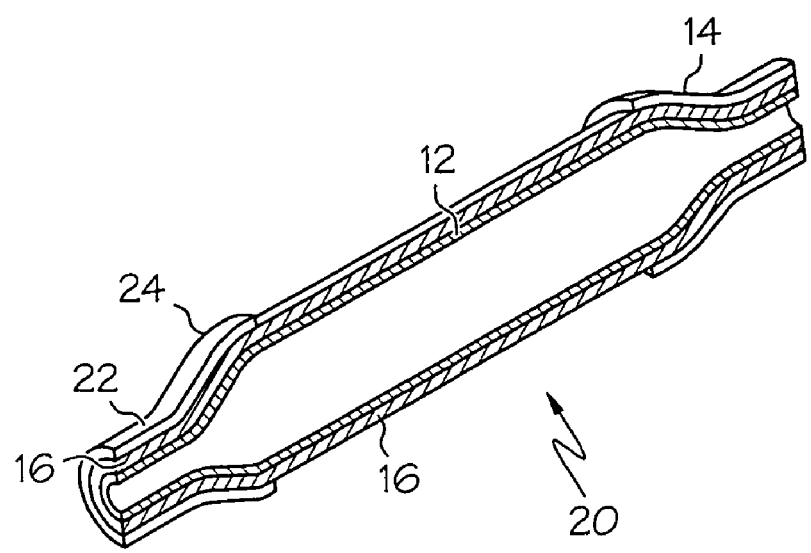
FIG. 8 is a sectional perspective view of an alternative multi layer construction of a dilatation balloon similar to that shown in FIG. 7.

FIG. 8 is a cross sectional perspective view of a multi layer dilatation balloon 20 according to the invention. In this embodiment, balloon 20 has a base layer 12 constructed from a first polymeric composition and a crosslinkable layer 14 disposed over waist 22 and cone 24 portions, and further has another layer 16 which may be a tie layer disposed over the entire surface of the base layer 12.

Figure 9:
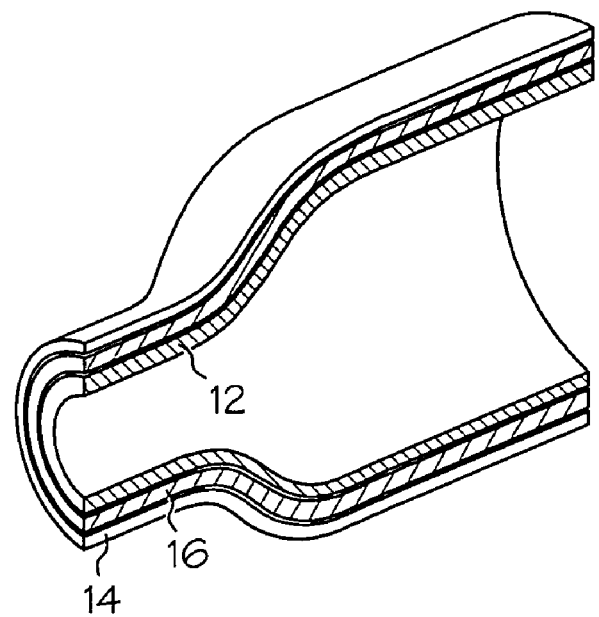
FIG. 9 is a sectional perspective view of an alternative construction of a dilatation balloon.

FIG. 9 shows an alternative construction of balloon 20 in which a base layer 12 of a first polymeric composition defines the balloon and the crosslinkable layer 14 of a second polymeric composition is coextensive with the base layer 12. This may be accomplished by coextrusion, among other techniques known to those of ordinary skill in the art. The techniques by which one layer may be applied over the other are numerous. In this embodiment, crosslinking may be limited to specific regions through the use of a crosslinking inhibitor, for example, or through selective application of an energy source to predetermined selective regions of the balloon structure.

In this embodiment, it is desirable to control the crosslink density, having higher crosslink density on the cones than on the body of the balloons. For example, the ratio of crosslink density on the body of the balloons to the cones is desirably about 1:1 to about 1:5. Crosslink density can be controlled in a number of ways including intensity and/or time of radiation, or by the use of crosslinking inhibitors. For example, crosslinking inhibitors may be employed at intermittent intervals along the tubular parison in order to control where crosslinking of the outer polymeric layer occurs. Of course, it may also be desirable to have virtually no crosslinking on some portions of the balloon structure as well.

Figure 10:
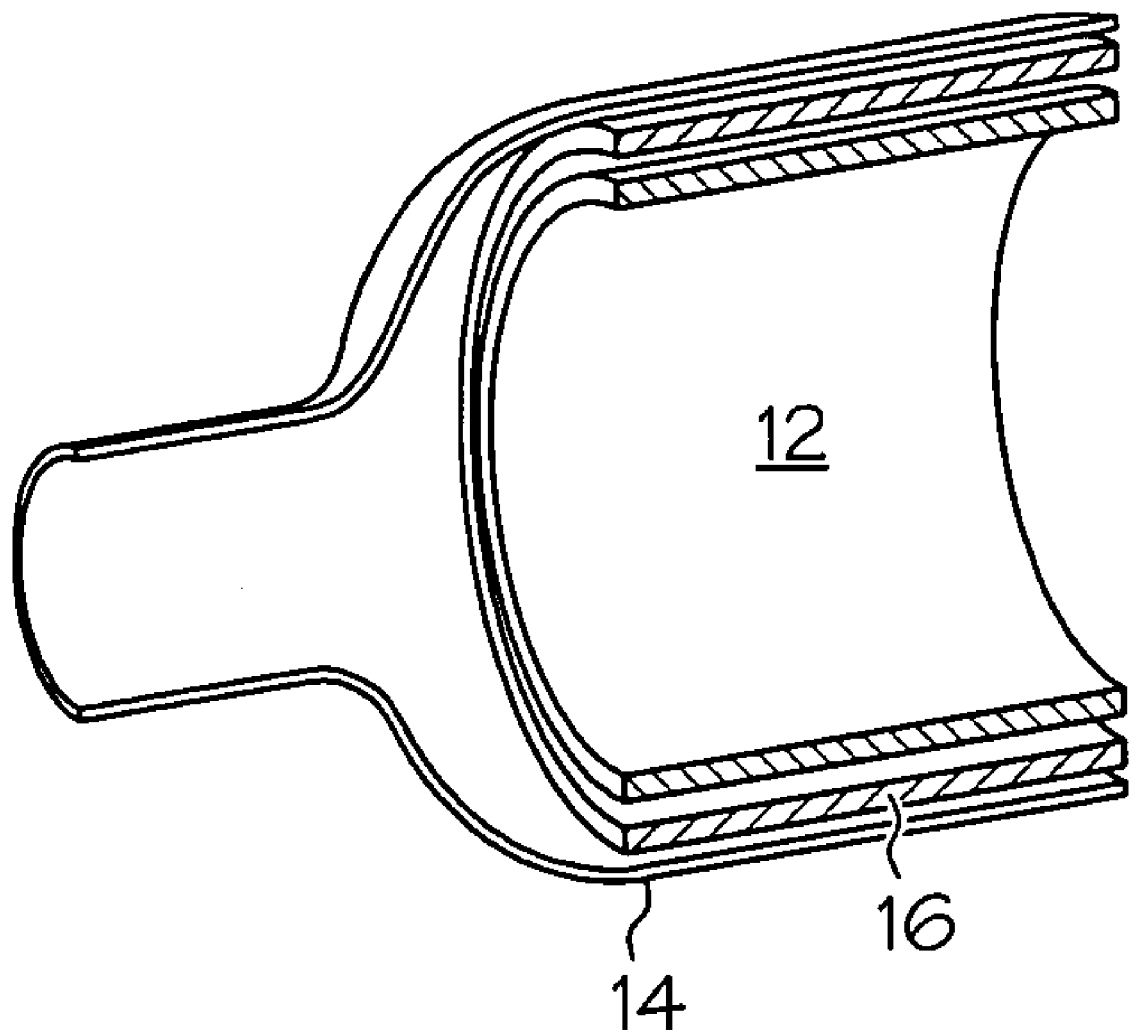
FIG. 10 is a cross sectional view of one embodiment of a multilayer balloon according to the invention.

FIG. 10 shows yet another alternative construction of a balloon 20 according to the invention. The outer layer 14 is the crosslinkable layer and the inner layer 12 is the base layer.

The crosslinkable layer in this embodiment again facilitates collapse of the balloon in the vasculature after use. Balloons having such a construction exhibit improved trackability, improved cross and recross, and improved rewrapping by providing a compressive forces in those regions. This can be further tailored on the proximal end to reduce the profile if necessary by adjusting the density of the crosslinking. Increasing the amount of crosslinking decreases the distance between molecules. Differential crosslinking can also be accomplished using photoinitiation or sensitization.

Thus, the present invention offers several advantages over currently employed methods including the ability to selectively and differentially crosslink the such that different compressive forces based not only on the amount of expansion of the tubular parison during balloon formation, but also by monitoring the amount of chemical agent and/or the intensity/time of the energy applied to effect crosslinking.

The present method also allows for exact placement of the crosslinkable layer and increases reproducibility of the bond length and the bond properties, and it exhibits a decrease in the cost of manufacturing and offers increased efficiency by the elimination of production steps.

The above disclosure is intended to be illustrative and not exhaustive. The description will suggest many variations and alternatives to those of ordinary skill in the art. All of these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A dilatation balloon for use in combination with a catheter device, said balloon having waist portions, cone portions and a body portion, said balloon formed of a first polymeric composition forming a first inner layer, said balloon having a second outer layer formed on at least a portion of said first layer of said balloon, said second layer comprising a second polymeric composition which is crosslinked to form a compression region on at least a portion of said balloon, said second polymeric composition is crosslinked on said waist portions, said cone portions, or both, and said second polymeric composition on said body portion is uncrosslinked.

2. The dilatation balloon of claim 1 further comprising a tie layer between said first layer and said second layer.

3. The dilatation balloon of claim 1 wherein said first polymeric composition comprises at least one member selected from the group consisting of polyolefins, polyesters, polyethers, polyamides, polyketones, polyvinyl chlorides, polyphenylene sulfides, polyurethanes, copolymers thereof and mixtures thereof.

4. The dilatation balloon of claim 3 further having a tie layer, said tie layer comprising polyethylene modified with at least one member selected from the group consisting of maleic anhydride, epoxies, oxazolines, carbodiimides, isocyanates, and mixtures thereof.

5. The dilatation balloon of claim 1 wherein said first layer comprises at least one member selected from the group consisting of polyether block amides, polyethylene terephthalate, polybutylene terephthalate, polyester-polyether block copolymers, and mixtures thereof.

6. The dilatation balloon of claim 1 said second polymeric composition comprising at least one member selected from the group of polyolefins.

7. The dilatation balloon of claim 1 wherein said first polymeric composition comprises a polyether block amide and said second polymeric composition comprises polyethylene.

8. The dilatation balloon of claim 1 wherein said balloon is further secured to a catheter shaft at said waist portions of said balloon.

9. The dilatation balloon of claim 8 wherein said second layer is removed after said balloon is secured to said catheter shaft.

10. The dilatation balloon of claim 8 further comprising a tie layer between said balloon and said catheter shaft.

11. The dilatation balloon of claim 10 wherein said tie layer further comprises a crosslinking inhibitor.

12. The dilatation balloon of claim 11 wherein said crosslinking inhibitor is a free radical scavenger.

13. The dilatation balloon of claim 10 wherein said tie layer is formed from a polymeric composition having a lower melting temperature than said first polymeric composition.

14. A dilatation balloon having first and second waist portions, first and second cone portions and a body portion, said dilatation balloon formed from a first polymeric composition that forms a first inner layer, said dilatation balloon further comprising a second outer layer on at least one of said first and second cone portions of said balloon formed from a second composition which is crosslinked to form a compression region, the entire body portion of the balloon is uncrosslinked.

* * * * *